(12) United States Patent
Kowalczyk et al.

(10) Patent No.: US 8,080,585 B2
(45) Date of Patent: Dec. 20, 2011

(54) ISOMALTULOSE WITH IMPROVED FLOWABILITY

(75) Inventors: Jörg Kowalczyk, Eisenberg/Steinborn (DE); Jörg Bernard, Albsheim (DE); Tillmann Dörr, Hohen-Sülzen (DE)

(73) Assignee: Sudzucker Aktiengesellschaft Mannheim-Ochsenfurt, Mannheim (DE)

(*) Notice: Subject to any disclaimer, the term of this patent is extended or adjusted under 35 U.S.C. 154(b) by 81 days.

(21) Appl. No.: 12/299,900

(22) PCT Filed: May 3, 2007

(86) PCT No.: PCT/EP2007/003883
§ 371 (c)(1),
(2), (4) Date: Nov. 6, 2008

(87) PCT Pub. No.: WO2007/128483
PCT Pub. Date: Nov. 15, 2007

(65) Prior Publication Data
US 2009/0209662 A1    Aug. 20, 2009

(30) Foreign Application Priority Data
May 8, 2006 (DE) .......... 10 2006 022 506

(51) Int. Cl.
*A01N 25/00* (2006.01)
*A23G 3/00* (2006.01)

(52) U.S. Cl. ........................... 514/777; 426/658
(58) Field of Classification Search ............ 514/777
See application file for complete search history.

(56) References Cited

U.S. PATENT DOCUMENTS 6,849,286 B1 * 2/2005 Bayerkohler et al. ........ 426/285

FOREIGN PATENT DOCUMENTS

| DE | 199 43 491 | 3/2001 |
| DE | 199 43 496 | 5/2001 |
| DE | 100 26 619 | 12/2001 |
| DE | 102004052800 | 5/2006 |
| EP | 1 550 666 | 7/2005 |
| JP | 60-204709 | 10/1985 |
| JP | 62-074276 | 4/1987 |
| JP | 03039100 | 2/1991 |

OTHER PUBLICATIONS

International Search Report for PCT/EP2007/003883. Aug. 23, 2007.
Preliminary Report on Patentability for PCT/EP2007/003883.

* cited by examiner

*Primary Examiner* — Sreeni Padmanabhan
*Assistant Examiner* — Timothy E Betton
(74) *Attorney, Agent, or Firm* — Bateman IP; Brett Peterson; Randall Bateman

(57) ABSTRACT

The invention concerns a crystalline isomaltulose product having improved flow properties as bulk product and no tendency toward long-time compaction, method for production of this product as well as a new use of isomaltulose.

21 Claims, No Drawings

ISOMALTULOSE WITH IMPROVED FLOWABILITY

RELATED APPLICATIONS

The present application is the U.S. National Phase of PCT Application PCT/EP2007/003883, filed 3 May 2007, claiming priority to German Patent Application No. 10 2006 022 506.6, filed 8 May 2006.

DESCRIPTION

The invention concerns a crystalline isomaltulose product, which as a bulk product has improved flow properties and does not tend to compact with time, a method for production of this product as well as a new application of isomaltulose.

BACKGROUND

Isomaltulose (also referred to as Palatinose®) is a disaccharide with α-1,6-glycoside linking of glucose and fructose (6-O-α-D-glucopyranosyl-fructofuranose). Isomaltulose is used in the food industry and pharmaceutical industry as a sweetener, vehicle and/or filler. An important area of application of isomaltulose is use of sucrose. Isomaltulose is often stored and processed like sucrose or other sugar substitutes in crystalline form as a loose bulk product. Crystalline isomaltulose, if possible, should have good storage capability and flow properties like other sugar substituents, in order to be fed to processing installations suitable and adapted for such substances without requiring major processing adjustments or design changes to the installations.

In contrast to other crystalline sugar substitutes isomaltulose is not very hygroscopic; high storage stability is expected accordingly. Unexpectedly, however, isomaltulose exhibits the disadvantageous effect of so-called "long-time compaction." In this phenomenon the isomaltulose crystals "cake together" to clumps or agglomerates. Such clumps or agglomerates hamper the flowability of the product during further processing. For example, isomaltulose is stored in sacks or so-called big packs and the content of the sacks fed to mechanical processing via filling hoppers or chutes. The formed agglomerates hamper emptying of the sacks and prevent flowing of the bulk product into the filing hoppers. Additional mechanical processing steps are therefore generally necessary in order to feed the stored and agglomerated isomaltulose to mechanical processing.

As an alternative, isomaltulose is stored in bulk product silos. Long-time compaction also occurs there. Isomaltulose therefore has a tendency toward shaft formation in core-flow silos. Silo storage of isomaltulose is seriously hampered and inexpedient in specific types of silos. Additional measures must be taken during silo storage, like periodic circulation within the silos.

Systematic studies show that massive long-time compaction occurs already after short storage times of about 48 hours. It was also found that further lengthening of the storage time over several days (for example 240 hours) only slightly increases the initial extent of long-time compaction. In comparison with other bulk products that are also known to have a tendency to agglomerate over time, the long-time compaction in isomaltulose occurs very quickly as a disadvantage. Long-time compaction of isomaltulose is also essentially independent of the usual moisture content of stored isomaltulose and the usual storage conditions. Moisture content and storage conditions disadvantageously do not have a sufficient effect on long-time compaction and flowability of isomaltulose. No ordinarily available storage conditions are known in which the undesired long-time compaction is adequately reduced.

There is a demand for obtaining crystalline isomaltulose as a bulk product in flowable and silo-storable form without disadvantageous long-time compaction occurring during storage.

In order to obtain flowability of bulk products for storage and processing in the food industry and in pharmaceuticals, so-called anticaking agents are generally added. Known anticaking agents include silicates, aluminosilicates, polysiloxanes, phosphates, sodium hydrogen carbonate or starch powder. A shortcoming of these auxiliaries is that they contaminate the initial product and/or have chemical properties that lead to drawbacks during processing of the product. It is also essential to declare such auxiliaries in the finished food product or pharmaceutical product.

DETAILED DESCRIPTION

Starting from the prior art, the technical problem to be solved by the present invention includes furnishing flowable crystalline isomaltulose that retains its flow capability and has no tendency to agglomerate over time without adding foreign substances and auxiliaries, like anticaking agents.

The technical problem also includes providing an improved anticaking agent that retains and improves the flowability of crystalline isomaltulose and similar products and reduces or suppresses the tendency toward long-time compaction.

The underlying technical problem is solved according to the invention by the furnishing of an isomaltulose product, a crystalline isomaltulose or isomaltulose composition that contains at least one to a maximum of 20 wt % (referred to the total dry substance content of the product) fine-powdered isomaltulose, i.e., isomaltulose fine fraction with a particle size of less than 100 µm, especially less than 50 µm. The isomaltulose composition may be made exclusively of isomaltulose.

The invention therefore includes providing a specific fraction of fine-powdered isomaltulose in known crystalline isomaltulose as can be obtained by isomerization from sucrose and crystallization. "Crystalline isomaltulose" is understood to mean a powdered granular bulk product of isomaltulose. Ordinary crystalline isomaltulose has isomaltulose crystals with a particle size of about 0.2 to 0.6 mm. "Fine-powdered isomaltulose" or "isomaltulose fine fraction" is understood to mean crystalline isomaltulose in powder form having a particle size of less than 100 µm, especially less 50 µm. In particular, this means that the fine-powdered isomaltulose has a specific particle size distribution. At a particle size distribution measured by means of the laser refraction method (instrument: Malvern Mastersizer 2000®) during dry dispersal in air with 0.6 bar dispersal pressure, a fine-powdered isomaltulose used according to the invention preferably has the following residue sums: 5% (d05)=about 44 µm, 50% (d50) =about 15 µm, 95% (d95)=about 1 µm (percentage is referred to volume percent). This means that only 5 vol % of the total particle volume is larger than about 44 µm. The fine-powdered isomaltulose therefore preferably has insignificant fractions, i.e., more than 95 vol % a particle size of less than 44 µm; in particular, the fine-powdered isomaltulose has a particle size of always less than 100 µm, especially less than 50 µm. A particle size of 100 µm or more then generally do not occur; its percentage is negligibly small, but especially less than 1 vol % and preferably less than 0.5 vol %.

Surprisingly, the isomaltulose fine fraction in the product proposed according to the invention means that the isomaltulose product, i.e., the crystalline isomaltulose or isomaltulose composition, no longer has a tendency toward disadvantageous long-time compaction during storage and permanently retains its flowability. As such, the advantageous effect is already strongly pronounced at an isomaltulose fine fraction of about 1 wt % in the total product. At a fine fraction of about 5 wt % the advantageous effect is maximal. At a fine fraction of more than about 20 wt %, the advantageous effect occurs in the background, in that the underlying technical problem can no longer be adequately solved. An isomaltulose fine fraction of 1 to 10 wt % is preferred; an isomaltulose fine fraction of 1 to 5 wt % (referred to total dry substance) is particularly preferred. An isomaltulose fine fraction of 1 to 4 wt % is especially preferred. An isomaltulose fine fraction of 1 to 3 wt % is especially preferred. An isomaltulose fine fraction of 1 to 2 wt % is especially preferred. An isomaltulose fine fraction of about 1 wt % is especially preferred.

In one variant, the crystalline isomaltulose in the isomaltulose product according to the invention without the fine fraction according to the invention has a crystal size of about 0.2 to about 0.6 mm, preferably about 0.3 to about 0.45 mm. This corresponds to the crystal size distribution of crystalline isomaltulose obtained from isomerization of sucrose and crystallization in known fashion.

Another variant of the invention is a crystalline isomaltulose that contains or preferably consists of an isomaltulose fine fraction with a particle size less than 100 μm, especially less than 50 μm, 1 to 5 wt % (referred to total dry substance) and a fraction of crystalline isomaltulose with a particle size about 0.3 to about 0.45 mm of 99 to 95 wt % (referred to total dry substance).

The isomaltulose product according to the invention may be pure isomaltulose. It is understood that other known auxiliaries, like anticaking agents, can additionally be added to the isomaltulose product according to the invention for further improvement of the processing capability.

Another object of the invention is therefore also a method for production of preferably pure, flowable, crystalline isomaltulose that especially has no tendency toward long-time compaction. The method according to the invention is characterized by the fact that crystalline isomaltulose obtainable preferably in the usual manner with a particle size of about 0.2 to about 0.6 mm, preferably 0.3 to about 0.45 mm, is combined with a fraction according to the invention of 1 to 20 wt %, preferably 1 to 10 wt %, especially 1 to 5 wt %, also especially 1 to 4 wt %, 1 to 3 wt %, 1 to 2 wt %, 1 wt % or (referred to total dry substance) fine isomaltulose, that is mixed, and a flowable, storage-stable crystalline isomaltulose product is thus obtained. It may be intensively mixed under agitation. Mixing occurs during production of the crystalline isomaltulose fraction or immediately before filling or storage. In another variant, the process parameters are chosen or additional expedients provided so that the fine fraction in the isomaltulose product proposed according to the invention is formed during preparation of the crystalline isomaltulose fraction or remains in the product once formed.

In each case, a pure isomaltulose product may be obtained, which, apart from ordinary contaminants, is generally isomaltulose.

Another object of the invention, however, is also a flowable and storage-stable isomaltulose-containing mixture that has fine fraction of isomaltulose according to the invention. In particular, this is a combination of isomaltulose with at least one additional carbohydrate, especially fructose, glucose, sucrose, trehalulose, isomaltose, isomelizitose, oligosaccharides with a degree of polymerization 3 or 4, preferably inulin and/or oligofructose, or carbohydrate alcohol, especially mannitol, sorbitol, xylitol, isomaltol or their mixtures. In one variant, the mixture contains isomaltulose and fructose or consists of them. In another variant, the mixture contains isomaltulose and glucose or consists of them, and in another variant, the mixture contains isomaltulose and sucrose or consists of them. In other variants, the mixture contains isomaltulose and trehalulose or consists of them; the mixture contains isomaltulose and isomaltose or consists of them; the mixture contains isomaltulose and isomelizitose or consists of them; or the mixture contains isomaltulose and oligosaccharides with a degree of polymerization of 3 or 4 or more or consists of them.

It was also found that fine-powdered isomaltulose can also be used in other similar, especially crystalline, bulk products to improve flowability and to prevent long-time compaction. It was found that the isomaltulose fine fraction according to the invention improves the processing capability or flowability of crystalline products, like sucrose, glucose, fructose, isomaltose as well as other solid, powdered mono-, di-, oligo-, polysaccharides and saccharide alcohols and possibly suppresses or reduces their tendency toward long-time compaction.

Another object of the invention is therefore also the use of fine-powdered isomaltulose as an anticaking agent in the bulk product. Another object of the invention is the use of fine-powdered isomaltulose as an anticaking agent in a bulk product. According to the invention the isomaltulose fine fraction is used in order to improve the flowability of a bulk product especially for mechanical processing and/or to retain it, especially during storage. The fine-powdered isomaltulose is preferably added to the bulk product as an anticaking agent in a percentage of 1 to 20 wt %, preferably 1 to 10 wt %, especially 1 to 5 wt %, with further preference 1 to 4 wt %, 1 to 3 wt %, 1 to 2 wt % or about 1 wt % (referred to total dry substance).

Some examples describing embodiments of the invention are included below.

PRACTICAL EXAMPLE

Storage Test of Isomaltulose

Isomaltulose batches from current production were investigated for use in the food industry. For this purpose the samples were aliquoted and all initially stored for 12 hours in a drying cabinet at 60° C. under vacuum. The water content and water activity ($a_W$-value) of the samples were then immediately determined. These values served as reference value (null sample).

The following storage conditions were chosen:
Storage temperature: 30° C.
45% relative humidity or 60% relative humidity
Storage time: three weeks
Storage without mechanical load (load only by the intrinsic weight of the sample);
Storage under additional mechanical load: 10 kg load on a circular surface of 10 cm diameter;
about 125 MPa a) Comparative Experiment The results of the storage test are shown in Table 1. The results show that after three weeks of storage no significant different relative to the null sample was found with respect to water content and water activity. Isomaltulose is not hygroscopic. Unexpectedly, however, clumping and agglomeration of the crystalline isomaltulose occurred.

TABLE 1

| Storage conditions (relative humidity) | Water content (%) | Water activity ($a_w$ value) | State of the sample |
|---|---|---|---|
| Null sample | 5.32 | 0.41 | Sample is fully flowable; no clumps |
| 45; without load | 5.33 | 0.43 | Clump formation occurs after a few days |
| 45; with load | 5.39 | 0.41 | Clump formation occurs after a few days; the effect is stronger under load than without load |
| 60; without load | 5.44 | 0.44 | Clump formation |
| 60; with load | 5.35 | 0.48 | Strong clump formation; the effect is stronger under load than without load | b) Isomaltulose with 5 wt % Fine Fraction (According to the Invention)

In another set of experiments the isomaltulose taken from current production was mixed with 5 wt % (referred to total dry substance content) fine-powdered isomaltulose with a particle size of less than 100 μm and thoroughly agitated.

The fine-powdered isomaltulose had the following particle sizes:

5 vol % (d05): 44 μm
50 vol % (d50): 15 μm
95 vol % (d95): 1 μm (laser refraction method; Malvern Mastersizer 2000®; dry dispersal in air; 0.6 bar dispersal pressure)

The samples were then aliquoted, null samples determined and stored for three weeks as described above (see a)). The results are shown in Table 2. Over the entire storage time of three weeks no noticeable clumping or agglomeration could be found in the bulk product. Even under load the sample still exhibited good flow properties. Any smaller clumps that formed were broken down without force.

TABLE 2

| Storage conditions (relative humidity) | Water content (%) | Water activity ($a_w$ value) | State of the sample |
|---|---|---|---|
| Null sample | 5.25 | 0.27 | Sample is fully flowable; no clumps |
| 45; without load | 5.15 | 0.39 | Sample is flowable; no clumps are formed |
| 45; with load | — | — | Samples are flowable; smaller clumps immediately break down |
| 60; without load | 5.15 | 0.45 | Samples are flowable; no clumps present |
| 60; with load | — | — | Samples are flowable; small clumps immediately break down | c) Isomaltulose with 20 wt % Fine Fraction (According to the Invention)

In another series of experiments the isomaltulose taken from current production with 20 wt % (referred to total dry substance content) fine-powdered isomaltulose with a particle size less than 100 μm (see b)) was mixed and thoroughly agitated. The samples were then aliquoted, null samples determined and stored as described above for three weeks.

The results are shown in Table 3. Even during addition of 20 wt % fine-powdered isomaltulose good flow properties were still found. Smaller formed clumps broke down without force. The crystalline isomaltulose in this form is flowable.

The flowability, however, is less than during addition of only 5 wt % fine-powdered isomaltulose (see b)).

TABLE 3

| Storage conditions (relative humidity) | Water content (%) | Water activity ($a_w$ value) | State of the sample |
|---|---|---|---|
| Null sample | 5.16 | 0.19 | Sample is fully flowable; no clumps |
| 45; without load | 5.19 | 0.39 | Sample is flowable; no clumps are formed |
| 45; with load | — | — | Samples are flowable; smaller present clumps immediately break down |
| 60; without load | 5.19 | 0.46 | Samples are flowable; no clumps present; moist impression |
| 60; with load | — | — | Samples are flowable; small clumps immediately break down; moist impression |

The invention claimed is:

1. A flowable powdered isomaltulose product comprising:
   an isomaltulose fine fraction with a particle size of less than about 100 μm, wherein the isomaltulose fine fraction comprises between about 1 percent and about 20 percent by weight of said product; and
   a powdered bulk material mixed with the isomaltulose fine fraction.

2. The isomaltulose product of claim 1 wherein the powdered bulk material is a carbohydrate.

3. The isomaltulose product of claim 1 wherein the isomaltulose fine fraction is between about 1 percent and about 10 percent by weight of said product.

4. The isomaltulose product of claim 1 wherein the isomaltulose fine fraction is between about 1 percent and about 5 percent by weight of said product.

5. A flowable powdered isomaltulose product comprising:
   an isomaltulose fine fraction with a particle size of less than about 100 μm the isomaltulose fine fraction comprising between about 1 weight percent and about 20 weight percent of said product; and
   a bulk saccharide fraction mixed with the isomaltulose fine fraction to form said product.

6. The isomaltulose product of claim 5 wherein the bulk saccharide fraction comprises crystalline isomaltulose having a crystal size between about 0.2 mm to about 0.6 mm.

7. The isomaltulose product of claim 6 wherein the isomaltulose fine fraction is between about 1 weight percent and about 10 weight percent of said product.

8. The isomaltulose product of claim 6 wherein the isomaltulose fine fraction is between about 1 weight percent and about 5 weight percent of said product.

9. The isomaltulose product of claim 6 wherein the crystalline isomaltulose has a crystal size from about 0.3 mm to about 0.45 mm.

10. The isomaltulose product of claim 5, wherein the bulk saccharide is selected from the group consisting of crystalline isomaltulose having a crystal size greater than about 0.2 mm, fructose, glucose, sucrose, isomaltose, and a carbohydrate alcohol.

11. The isomaltulose product of claim 5, wherein the bulk saccharide is crystalline.

12. The isomaltulose product of claim 5 wherein the isomaltulose fine fraction is between about 1 weight percent and about 5 weight percent of said product, and wherein the bulk saccharide comprises coarse crystalline isomaltulose comprising between about 95 weight percent and about 1 weight percent of said product.

13. A method for producing a flowable isomaltulose product comprising the steps of:
- selecting an isomaltulose fine fraction with a particle size of less than about 100 μm;
- selecting a crystalline isomaltulose coarse fraction with a crystal size of greater than about 0.2 mm;
- mixing said isomaltulose fine fraction with said crystalline isomlatulose coarse fraction; and
- wherein mixing the isomaltulose fine fraction with the crystalline isomaltulose coarse fraction improves the flowable properties of the isomaltulose product and prevents clump formation.

14. The method of claim 13 wherein the crystalline isomaltulose coarse fraction has a particle size from about 0.2 mm to about 0.6 mm.

15. The method of claim 13 wherein the crystalline isomaltulose coarse fraction has a particle size from about 0.3 mm to about 0.45 mm.

16. The method of claim 13 wherein the isomaltulose fine fraction is between about 1 percent and about 20 percent by weight of said product.

17. The method of claim 13 wherein the isomaltulose fine fraction is between about 1 percent and about 10 percent by weight of said product.

18. The method of claim 13 wherein the isomaltulose fine fraction is between about 1 percent and about 5 percent by weight of said product.

19. The isomaltulose product of claim 1 wherein the powdered bulk material comprises coarse crystalline isomaltulose having a crystal size greater than about 0.2 mm.

20. The isomaltulose product of claim 19 wherein the isomaltulose fine fraction comprises between about 1 percent and about 5 percent by weight of said product, and wherein the coarse crystalline isomaltulose comprises between about 95 percent and about 99 percent by weight of said product.

21. The isomaltulose product of claim 1 wherein the powdered bulk material is crystalline.

\* \* \* \* \*